United States Patent
Prinzen et al.

(10) Patent No.: US 7,979,123 B2
(45) Date of Patent: Jul. 12, 2011

(54) INTERMITTENT STRESS AUGMENTATION PACING FOR CARDIOPROTECTIVE EFFECT

(75) Inventors: Frits Prinzen, Maastricht (NL);
Richard Cornelussen, Maastricht (NL);
Ward Vanagt, Maastricht (NL); Joseph M. Pastore, Woodbury, MN (US); Julio C. Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 471 days.

(21) Appl. No.: 11/868,767

(22) Filed: Oct. 8, 2007

(65) Prior Publication Data

US 2008/0027495 A1    Jan. 31, 2008

Related U.S. Application Data

(63) Continuation of application No. 11/030,575, filed on Jan. 6, 2005, now Pat. No. 7,295,874.

(51) Int. Cl.
*A61N 1/362* (2006.01)
*A61N 1/18* (2006.01)
*A61B 5/04* (2006.01)

(52) U.S. Cl. ............... 607/17; 607/9; 607/27; 600/510; 600/515; 600/516; 600/517

(58) Field of Classification Search ............... 607/9, 17, 607/27; 600/510, 515, 516, 517
See application file for complete search history.

(56) References Cited

U.S. PATENT DOCUMENTS

| | | | |
|---|---|---|---|
| 4,834,710 A | 5/1989 | Fleck | |
| 4,919,133 A | 4/1990 | Chiang | |
| 5,072,458 A | 12/1991 | Suzuki | |
| 5,111,818 A | 5/1992 | Suzuki et al. | |
| 5,127,404 A | 7/1992 | Wyborny et al. | |
| 5,135,004 A | 8/1992 | Adams et al. | |
| 5,178,618 A | 1/1993 | Kandarpa | |
| 5,184,615 A | 2/1993 | Nappholz et al. | |
| 5,190,035 A | 3/1993 | Salo et al. | |
| 5,199,428 A | 4/1993 | Obel et al. | |
| 5,282,840 A | 2/1994 | Hudrlik et al. | |
| 5,484,419 A | 1/1996 | Fleck | |
| 5,531,768 A | 7/1996 | Alferness | |
| 5,588,432 A | 12/1996 | Crowley | |

(Continued)

FOREIGN PATENT DOCUMENTS

WO    WO-95/18649 A1    7/1995

(Continued)

OTHER PUBLICATIONS

"U.S. Appl. No. 11/030,575, Response filed Oct. 26, 2006 to Non Final Office Action mailed Jul. 26, 2006", 8 pgs.

(Continued)

*Primary Examiner* — Carl H Layno
*Assistant Examiner* — Natasha N Patel
(74) *Attorney, Agent, or Firm* — Schwegman, Lundberg & Woessner, P.A.

(57) ABSTRACT

A device and method for delivering electrical stimulation to the heart in a manner which provides a protective effect against subsequent ischemia is disclosed. The protective effect is produced by configuring a cardiac pacing device to intermittently switch from a normal operating mode to a stress augmentation mode in which the spatial pattern of depolarization is varied to thereby subject a particular region or regions of the ventricular myocardium to increased mechanical stress.

20 Claims, 3 Drawing Sheets

U.S. PATENT DOCUMENTS

| | | | |
|---|---|---|---|
| 5,634,899 | A | 6/1997 | Shapland et al. |
| 5,755,671 | A | 5/1998 | Albrecht et al. |
| 5,814,089 | A | 9/1998 | Stokes et al. |
| 5,817,131 | A | 10/1998 | Elsberry et al. |
| 5,833,603 | A | 11/1998 | Kovacs et al. |
| 5,876,433 | A | 3/1999 | Lunn |
| 5,906,636 | A | 5/1999 | Casscells, III et al. |
| 5,919,209 | A | 7/1999 | Schouten |
| 6,021,350 | A | 2/2000 | Mathson |
| 6,108,577 | A | 8/2000 | Benser |
| 6,115,628 | A | 9/2000 | Stadler et al. |
| 6,233,486 | B1 | 5/2001 | Ekwall et al. |
| 6,256,233 | B1 | 7/2001 | Glass |
| 6,256,538 | B1 | 7/2001 | Ekwall |
| 6,272,379 | B1 | 8/2001 | Fischell et al. |
| 6,278,894 | B1 | 8/2001 | Salo et al. |
| 6,285,907 | B1 | 9/2001 | Kramer et al. |
| 6,368,284 | B1 | 4/2002 | Bardy |
| 6,445,953 | B1 | 9/2002 | Bulkes et al. |
| 6,477,402 | B1 | 11/2002 | Lynch et al. |
| 6,501,983 | B1 | 12/2002 | Natarajan et al. |
| 6,511,477 | B2 | 1/2003 | Altman et al. |
| 6,569,145 | B1 | 5/2003 | Shmulewitz et al. |
| 6,584,362 | B1 | 6/2003 | Scheiner et al. |
| 6,604,000 | B2 | 8/2003 | Lu |
| 6,610,713 | B2 | 8/2003 | Tracey |
| 6,628,988 | B2 | 9/2003 | Kramer et al. |
| 6,711,436 | B1 | 3/2004 | Duhaylongsod |
| 6,813,516 | B2 * | 11/2004 | Ujhelyi et al. ............. 607/4 |
| 6,827,690 | B2 | 12/2004 | Bardy |
| 6,838,471 | B2 | 1/2005 | Tracey |
| 6,842,642 | B2 | 1/2005 | Vanhout |
| 6,865,420 | B1 | 3/2005 | Kroll |
| 6,892,095 | B2 | 5/2005 | Salo |
| 6,907,285 | B2 | 6/2005 | Denker et al. |
| 6,913,577 | B2 | 7/2005 | Bardy |
| 6,937,899 | B2 | 8/2005 | Sheldon et al. |
| 6,950,701 | B2 * | 9/2005 | Begemann et al. ............ 607/9 |
| 6,973,349 | B2 | 12/2005 | Salo |
| 7,039,462 | B2 | 5/2006 | Pastore et al. |
| 7,043,305 | B2 | 5/2006 | Kenknight et al. |
| 7,062,325 | B1 | 6/2006 | Krig et al. |
| 7,069,070 | B2 | 6/2006 | Carlson et al. |
| 7,215,997 | B2 | 5/2007 | Yu et al. |
| 7,295,874 | B2 | 11/2007 | Prinzen et al. |
| 7,299,087 | B2 | 11/2007 | Bardy |
| 7,340,303 | B2 | 3/2008 | Zhu |
| 7,364,547 | B2 | 4/2008 | Stahmann et al. |
| 7,366,568 | B2 | 4/2008 | Pastore et al. |
| 7,437,191 | B2 | 10/2008 | Pastore et al. |
| 7,460,906 | B2 | 12/2008 | Libbus |
| 7,479,112 | B2 | 1/2009 | Sweeney et al. |
| 7,486,991 | B2 | 2/2009 | Libbus et al. |
| 2002/0042632 | A1 | 4/2002 | Iaizzo et al. |
| 2002/0072777 | A1 | 6/2002 | Lu |
| 2002/0082660 | A1 | 6/2002 | Stahmann et al. |
| 2003/0004549 | A1 | 1/2003 | Hill et al. |
| 2003/0009189 | A1 | 1/2003 | Gilson et al. |
| 2003/0045800 | A1 | 3/2003 | Condie et al. |
| 2003/0055461 | A1 | 3/2003 | Girouard et al. |
| 2003/0060854 | A1 | 3/2003 | Zhu |
| 2003/0120313 | A1 | 6/2003 | Begemann et al. |
| 2003/0120315 | A1 | 6/2003 | Spinelli et al. |
| 2003/0139778 | A1 | 7/2003 | Fischell et al. |
| 2003/0158492 | A1 | 8/2003 | Sheldon et al. |
| 2003/0158584 | A1 | 8/2003 | Cates et al. |
| 2003/0204206 | A1 | 10/2003 | Padua et al. |
| 2003/0204231 | A1 | 10/2003 | Hine et al. |
| 2003/0233130 | A1 | 12/2003 | Padmanabhan et al. |
| 2004/0015081 | A1 | 1/2004 | Kramer et al. |
| 2004/0038947 | A1 | 2/2004 | Wink et al. |
| 2004/0049235 | A1 | 3/2004 | Deno et al. |
| 2004/0088017 | A1 | 5/2004 | Sharma et al. |
| 2004/0102815 | A1 | 5/2004 | Balczewski et al. |
| 2004/0133247 | A1 | 7/2004 | Stahmann et al. |
| 2004/0255956 | A1 | 12/2004 | Vinten-Johansen et al. |
| 2005/0075673 | A1 | 4/2005 | Warkentin et al. |
| 2005/0143779 | A1 | 6/2005 | Libbus |
| 2005/0143780 | A1 * | 6/2005 | Henry et al. ............... 607/9 |
| 2005/0149129 | A1 | 7/2005 | Libbus et al. |
| 2005/0261741 | A1 | 11/2005 | Libbus et al. |
| 2005/0288721 | A1 | 12/2005 | Girouard et al. |
| 2006/0241704 | A1 | 10/2006 | Shuros et al. |
| 2007/0162081 | A1 | 7/2007 | Yu et al. |

FOREIGN PATENT DOCUMENTS

| | | | |
|---|---|---|---|
| WO | WO-01/15609 | A1 | 3/2001 |
| WO | WO-2004/058326 | A2 | 7/2004 |
| WO | WO-2006/074189 | A1 | 7/2006 |

OTHER PUBLICATIONS

"U.S. Appl. No. 11/030,575, Non-Final Office Action mailed Jul. 26, 2006", 10 pgs.

"U.S. Appl. No. 11/030,575, Notice of Allowance mailed Jan. 17, 2007", 7 pgs.

"U.S. Appl. No. 11/030,575, Notice of Allowance mailed Jun. 7, 2007", 7 pgs.

"International Application Serial No. PCT/US2006/000125, International Search Report and Written Opinion mailed May 11, 2006", 12 pgs.

Baynham, T. C, "Method and Apparatus for Cardiac Protection Pacing", U.S. Appl. No. 11/129,050, filed May 13, 2005, 33 pgs.

Baynham, T. C, et al., "Method and Apparatus for Initiating and Delivering Cardiac Protection Pacing", U.S. Appl. No. 11/382,849, filed May 11, 2006, 37 pgs.

Dzwonczyk, R., et al., "Myocardial Electrical Impedance Responds to Ischemia and Reperfusion in Humans", *IEEE Transactions on Biomedical Engineering*, 51(12), (Dec. 2004), 2206-2209.

Girouard, S. D., "Pulmonary Vein Stent for Treating Atrial Fibrillation", U.S. Appl. No. 60/298,741, filed Jun. 15, 2001, 14 pgs.

Ishihara, M., et al., "Implications of prodromal angina pectoris in anterior wall acute myocardial infarction: acute angiographic findings and long-term prognosis", *J Am Coll Cardiol.*, 30(4), (1997), 970-975.

Kis, A., "Repeated cardiac pacing extends the time during which canine hearts are protected against ischaemia-induced arrhythmias : role of nitric oxide.", *Journal of Molecular and Cellular Cardiology*, 31(6), (1999), 1229-1241.

Kloner, R. A., et al., "Prospective temporal analysis of the onset of preinfarction angina versus outcome: an ancillary study in TIMI-9B", *Circulation*, 97(11), (1998), 1042-1045.

Koning, M. M. G., et al., "Rapid Ventricular Pacing Produces Myocardial Protection by Nonischemic Activation of $K_{ATP}^+$ Channels", *Circulation*, 93(1), (Jan. 1, 1996), 178-186.

Krayenbuhl, H. P., "Hemodynamics in ischemia. Systolic phase", *Z. Kardiol.*, 73 Suppl 2, [Article in German with English Abstract], (1984), 119-25.

Meier, B., et al., "Coronary Pacing During Percutaneous Transluminal Coronary Angioplasty", *Therapy And Prevention Cardiac Pacing*, 71(3), (Mar. 1985), 557-561.

Murry, C. E., "Preconditioning with ischemia: a delay of lethal cell injury in ischemic myocardium", *Circulation*, 74(5), (1986), 1124-1136.

Ovize, M., et al., "Stretch preconditions canine myocardium.", *Am J Physiol.*, 266(1 Pt 2), (Jan. 1994), H137-46.

Pastore, J. M., "Delivery of Intermittent Stress Augmentation Paging for Cardioprotective Effect", U.S. Appl. No. 11/151,015, filed Jun. 13, 2005 25 pgs.

Pastore, J. M., et al., "Intermittent Stress Augmentation Pacing for Cardioprotective Effect", U.S. Appl. No. 11/458,286, filed Jul. 18, 2006, 23 pgs.

Pastore, Joseph M, et al., "Method and Apparatus for Delivering Pacing Pulses Using a Coronary Stent", U.S. Appl. No. 11/129,058, filed May 13, 2005, 34 pgs.

Prinzen, F. W., "Mapping of regional myocardial strain and work during ventricular pacing: experimental study using magnetic resonance imaging tagging", *Journal of the American College of Cardiology*, 33(6), (May 1999), 1735-1742.

Solomon, S. D., et al., "Angina pectoris prior to myocardial infarction protects against subsequent left ventricular remodeling", *J Am Coll Cardiol.*, 43(9), (2004), 1511-1514.

Vegh, A., et al., "Transient ischaemia induced by rapid cardiac pacing results in myocardial preconditioning", *Cardiovascular Research*, 25(12), (Dec. 1991), 1051-1053.

Zhao, Zhi-Qing, et al., "Inhibition of myocardial injury by ischemic postconditioning during reperfusion: comparison with ischemic preconditioning", *Am J Physiol Heart Circ Physiol*, 285(2), (Aug. 2003), H579-H588.

"European Application Serial No. 06717345.0, Communication dated Aug. 22, 2007", 2 pgs.

"European Application Serial No. 06717345.0, Office Action mailed May 15, 2009", 2 pgs.

"European Application Serial No. 06717345.0, Response filed Sep. 11, 2009 to Communication mailed May 15, 2009", 7 pgs.

"European Application Serial No. 06717345.0, Response filed Sep. 28, 2007 to Communication dated Aug. 22, 2007", 12 pgs.

"International Application Serial No. PCT/US2006/000125, International Search Report mailed May 11, 2006", 4 pgs.

"International Application Serial No. PCT/US2006/000125, Written Opinion mailed May 11, 2006", 6 pgs.

"U.S. Appl. No. 11/113,828, Non-Final Office Action mailed Mar. 5, 2008", 8 pgs.

"U.S. Appl. No. 11/113,828, Response filed Mar. 23, 2009 to Non-Final Office Action mailed Dec. 22, 2008", 8 pgs.

"U.S. Appl. No. 11/113,828, Response filed Jun. 5, 2008 to Non-Final Office Action mailed Mar. 5, 2008", 8 pgs.

"U.S. Appl. No. 11/113,828, Response filed Nov. 17, 2008 to Final Office Action mailed Sep. 17, 2008", 11 pgs.

"U.S. Appl. No. 11/129,050, Response filed Feb. 23, 2009 to Non-Final Office Action mailed Nov. 6, 2008", 13 pgs.

"U.S. Appl. No. 11/129,050, Response filed Jul. 14, 2008 to Final Office Action mailed May 12, 2008", 13 pgs.

Airaksinen, K. E., et al., "Antiarrhythmic effect of repeated coronary occlusion during balloon angioplasty", J Am Coll Cardiol., 29(5), (Apr. 1997), 1035-1038.

Brunner, Friedrich, "Attenuation of myocardial ischemia/reperfusion injury in mice with myocyte-specific overexpression of endothelial nitric oxide synthase", Cardiovascular Research, 57, (2003), 55-62.

Gewaltig, Michael T, "Vasoprotection by nitric oxide: mechanisms and therapeutic potential", Cardiovascular Research, 55, (Feb. 14, 2002), 250-260.

Kin, Hajime, et al., "Postconditioning attenuates myocardial ischemia-reperfusion injury by inhibiting events in the early minutes of reperfusion", Cardiovascular Research, 62(1), (Apr. 1, 2004), 74-85.

Loukogeorgakis, S. P., et al., "Remote ischemic preconditioning provides early and late protection against endothelial ischemia-reperfusion injury in humans: role of the autonomic nervous system.", J Am Coll Cardiol., 46(3), (Aug. 2, 2005), 450-6.

Paolocci, Nazareno, et al., "Positive inotropic and lusitropic effects of HNO/NO- in failing hearts: Independence from beta-adrenergic signaling", Proceedings of the National Academy of Sciences USA, 100(9), (Apr. 29, 2003), 5537-5542.

Schoemaker, R. G., et al., "Bradykinin mediates cardiac preconditioning at a distance", Am J Physiol Heart Circ Physiol., 278(5), (May 2000), H1571-6.

Tsang, A., et al., "Postconditioning: a form of "modified reperfusion" protects the myocardium by activating the phosphatidylinositol 3-kinase Akt pathway", Circ Res., 95(3), Epub Jul. 8, 2004 (Aug. 6, 2004), 230-2.

Vanagt, W. Y. R., et al., "Ventricular Pacing for Improving Myocardial Tolerance to Ischemia", Progress Report on Project Guidant-CARIM, (Oct. 2003), 1-25.

Woldbaek, Per Raidar, et al., "Increaesed cardia IL-18 mRNA, pro-IL 18 and plasma IL-18 after myocardial infarction in the mouse; a potential role in cardiac dysfunction", Cardiovascular Research, 59, (2003), 122-131.

Wolfrum, Sebastian, et al., "Acute Reduction of Myocardial Infarct Size By a Hydroxymethyl Glutaryl Coenzyme A Reductase Inhibitor Is Mediated By Endothelial Nitric Oxide Synthase", J. Cardiocas Pharmacol, vol. 41, No. 3, (Mar. 2003), 474-480.

Wu, Zhong-Kai, et al., "Ischemic preconditioning suppresses ventricular tachyarrhythmias after myocardial revascularization", Circulation, 106(24), (Dec. 10, 2002), 3091-3096.

Wunderlich, Carsten, "Acute Inhibition of Myoglobin Impairs Contractility and Energy State of iNOS-Overexpressing Hearts", Circulation Research, 92, (2003), 1352-1358.

Yang, S. M., et al., "Multiple, brief coronary occlusions during early reperfusion protect rabbit hearts by targeting cell signaling pathways", Journal of the American College of Cardiology, 44(5), (Sep. 1, 2004), 1103-1110.

\* cited by examiner

INTERMITTENT STRESS AUGMENTATION PACING FOR CARDIOPROTECTIVE EFFECT

CROSS REFERENCE TO RELATED APPLICATION

This application is a continuation of U.S. application Ser. No. 11/030,575, filed Jan. 6, 2005, now U.S. Pat. No. 7,295,874 the specification of which is herein incorporated by reference.

FIELD OF THE INVENTION

This invention pertains to apparatus and methods for the treatment of heart disease and to devices providing electro-stimulation to the heart such as cardiac pacemakers.

BACKGROUND

Coronary artery disease (CAD) occurs when the coronary arteries that supply blood to the heart muscle become hardened and narrowed due to atherosclerosis. The arteries harden and become narrow due to the buildup of plaque on the inner walls or lining of the arteries. Blood flow to the heart is reduced as plaque narrows the coronary arteries. This decreases the oxygen supply to the heart muscle. CAD is the most common type of heart disease, which is the leading cause of death in the U.S. in both men and women.

An atherosclerotic plaque is the site of an inflammatory reaction within the wall of an artery and is made up of a core containing lipid and inflammatory cells surrounded by a connective tissue capsule. A myocardial infarction (MI), or heart attack, occurs when atherosclerotic plaque within a coronary artery ruptures and leads to the clotting of blood (thrombosis) within the artery by exposing the highly thrombogenic lipid core of the plaque to the blood. The complete or nearly complete obstruction to coronary blood flow can damage a substantial area of heart tissue and cause sudden death, usually due to an abnormal heart rhythm that prevents effective pumping.

Besides causing an MI, CAD can also produce lesser degrees of cardiac ischemia due to the narrowing of a coronary artery lumen by atherosclerotic plaque. When blood flow and oxygen supply to the heart is reduced, patients often experience chest pain or discomfort, referred to as angina pectoris. Angina pectoris serves as a useful warning of insufficient myocardial perfusion which can lead to the more serious situation such as a heart attack or cardiac arrhythmia. Patients who experience anginal episodes are commonly treated either with medication or by surgical revascularization. It has also been found, however, that patients who experience anginal episodes prior to a heart attack often have a lower mortality rate than heart attack patients who do not experience such episodes. It is theorized that this phenomenon may be due to ischemic preconditioning of the heart by the anginal episodes which thereby renders the myocardial tissue less likely to become infarcted if blood supply is sharply reduced by a subsequent coronary thrombus.

DETAILED DESCRIPTION

The present disclosure relates to a method and device which employs pacing therapy to precondition the heart to be less vulnerable to sudden reductions in blood flow. It has been found that intermittent pacing of the heart results in a cardioprotective effect which renders the myocardium more resistant (i.e., less likely to become infarcted) during a subsequent episode of myocardial ischemia. As explained below, pacing therapy may be applied in such a manner that certain regions of the ventricular myocardium are subjected to an increased mechanical stress. It is believed that the increased myocardial stress preconditions the heart to better withstand the effects of subsequent ischemia through a signal transduction cascade which causes the release of certain cellular constituents and/or induces expression of particular genes. The mechanism responsible for the cardioprotective effect of increased stress may or may not be similar to the mechanism by which prior ischemia preconditions the heart. It has been experimentally observed in animal studies, however, that pacing therapy causing increased stress to a particular region of the myocardium can produce a cardioprotective effect without making the region ischemic.

Described below is an exemplary device for delivering pacing therapy in a manner which preconditions the heart to better withstand subsequent ischemia, referred to herein as intermittent stress augmentation pacing. Also set forth is an explanation as to how pacing may produce increased mechanical stress to a myocardial region and an exemplary pacing algorithm.

1. Mechanical Effects of Pacing Therapy

The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts does so against a lower afterload than does a part of the ventricle contracting later. The degree to which a heart muscle fiber is stretched before it contracts is termed the preload. The maximum tension and velocity of shortening of a muscle fiber increases with increasing preload, and the increase in contractile response of the heart with increasing preload is known as the Frank-Starling principle. When a myocardial region contracts late relative to other regions, the earlier contraction of opposing regions stretches the later contracting region and increases its preload. Thus, a myocardial region which contracts later than other regions during systole is subjected to both an increased preload and an increased afterload, both of which cause the region to experience increased wall stress.

When the ventricles are stimulated to contract by a pacing pulse applied through an electrode located at a particular pacing site, the excitation spreads from the pacing site by conduction through the myocardium. This is different from the normal physiological situation, where the spread of excitation to the ventricles from the AV node makes use of the heart's specialized conduction system made up of Purkinje fibers which allows a rapid and synchronous excitation of the entire ventricular myocardium. The excitation resulting from a pacing pulse applied to a single site, on the other hand, produces a relatively asynchronous contraction owing to the slower velocity at which excitation is conducted through the myocardium. Regions of the myocardium located more distally from the pacing site are excited later than regions proximal to the pacing site and, for the reasons explained above, subjected to increased mechanical stress.

The ventricular contractions resulting from pacing pulses are thus generally not as synchronized as intrinsic contractions and may therefore be hemodynamically less efficient. For example, in conventional bradycardia pacing, the pacing site is located in the right ventricle so that excitation must spread from the right ventricular pacing site through the rest the myocardium. The left ventricular contraction then occurs in a less coordinated fashion than in the normal physiological situation which can reduce cardiac output. This problem can be overcome by pacing the left ventricle, either in addition to or instead of the right ventricle, to produce a more coordinated ventricular contraction, referred to as cardiac resynchronization pacing. Resynchronization pacing, besides overcoming the desynchronizing effects of conventional pacing therapy, may also be applied to patients who suffer from intrinsic ventricular conduction deficits in order to improve the efficiency of ventricular contractions and increase cardiac output. Ventricular resynchronization therapy may be delivered as left ventricle-only pacing, biventricular pacing, or pacing delivered to multiple sites in either or both ventricles.

In contradistinction to resynchronization therapy, pacing therapy delivered to produce a cardioprotective effect is pacing which is intended to produce a relatively asynchronous contraction so that myocardial regions located more distally from the pacing site are subjected to increased mechanical stress. Such pacing, referred to as stress augmentation pacing, produces a pattern of myocardial depolarization which is different from the dominant or chronic depolarization pattern resulting from intrinsic or paced activation. If stress augmentation pacing is delivered on a relatively constant basis, however, the later contracting ventricular regions can undergo hypertrophy and other remodeling processes in response to the increased stress, and such remodeling can counteract the cardioprotective effects. The effectiveness of stress augmentation pacing is therefore increased if such pacing is delivered as a single treatment or multiple treatments spread over some period of time so that remodeling does not occur. Stress augmentation pacing may be delivered by a variety of means. In one embodiment, an external pacing device delivers pacing pulses to the heart via pacing electrodes which are incorporated into a catheter which may be disposed near the heart. Such a catheter may be one which is also used for other types of cardiac treatment or diagnosis such as angiography or angioplasty. Stress augmentation pacing may also be delivered by an implantable pacing device. As described below, a cardiac pacing device may be programmed to deliver pacing which stresses a particular myocardial region on an intermittent basis. The device may also be configured to intermittently pace multiple pacing sites in order to provide a cardioprotective effect to multiple myocardial regions.

2. Exemplary Cardiac Device

Cardiac rhythm management devices such as pacemakers are usually implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
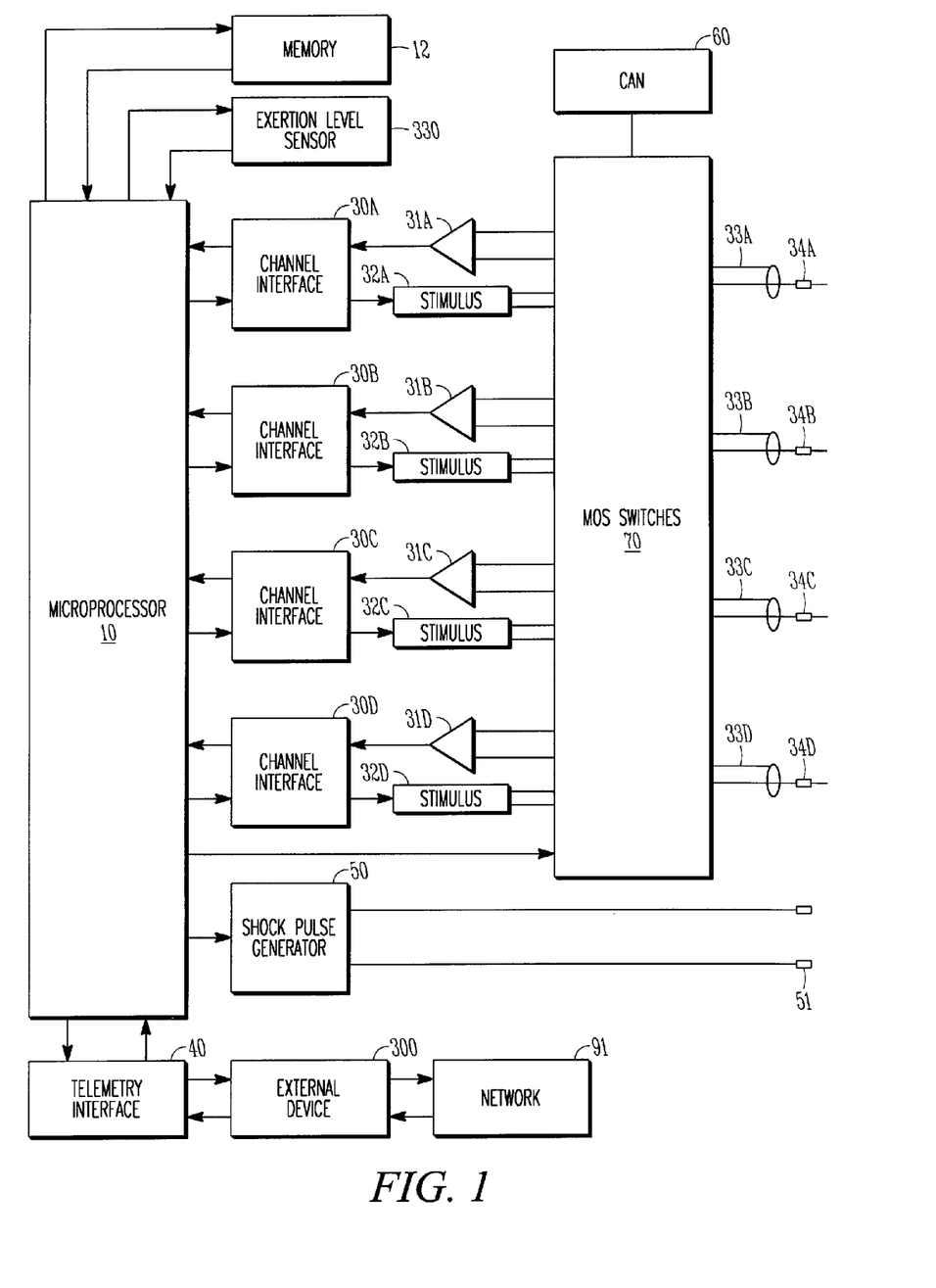
FIG. 1 is a block diagram of an exemplary cardiac rhythm management device for practicing the present invention.

FIG. 1 shows a system diagram of a microprocessor-based cardiac rhythm management device or pacemaker suitable for practicing the present invention. The controller of the pacemaker is a microprocessor 10 which communicates with a memory 12 via a bidirectional data bus. The memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

The device is equipped with multiple electrodes each of which may be incorporated into a pacing and/or sensing channel. Shown in the figure are four exemplary sensing and pacing channels designated "a" through "d" comprising bipolar leads with ring electrodes 34*a-d* and tip electrodes 33*a-d*, sensing amplifiers 31*a-d*, pulse generators 32*a-d*, and channel interfaces 30*a-d*. Each channel thus includes a pacing channel made up of the pulse generator connected to the electrode and a sensing channel made up of the sense amplifier connected to the electrode. By appropriate placement of the electrode, a channel may be configured to sense and/or pace a particular atrial or ventricular site. The channel interfaces 30*a-d* communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 60 serving as a ground electrode. As explained below, one way in which the device may alter the spatial distribution of pacing is to switch from unipolar to bipolar pacing (or vice-versa) or to interchange which electrodes of a bipolar lead are the cathode and anode during bipolar pacing. A shock pulse generator 50 is also interfaced to the controller for delivering a defibrillation shock via a pair of shock electrodes 51 to the atria or ventricles upon detection of a shockable tachyarrhythmia.

The controller controls the overall operation of the device in accordance with programmed instructions stored in memory, including controlling the delivery of paces via the pacing channels, interpreting sense signals received from the sensing channels, and implementing timers for defining escape intervals and sensory refractory periods. An exertion level sensor 330 (e.g., an accelerometer, a minute ventilation sensor, or other sensor that measures a parameter related to metabolic demand) enables the controller to adapt the pacing rate in accordance with changes in the patient's physical activity. A telemetry interface 40 is also provided which enables the controller to communicate with an external device 300 such as an external programmer via a wireless telemetry link. An external programmer is a computerized device with an associated display and input means that can interrogate the pacemaker and receive stored data as well as directly adjust the operating parameters of the pacemaker. The external device 300 shown in the figure may also be a remote monitoring unit. The external device 300 may also be interfaced to a patient management network 91 enabling the implantable device to transmit data and alarm messages to clinical personnel over the network as well as be programmed remotely. The network connection between the external device 300 and the patient management network 91 may be implemented by, for example, an internet connection, over a phone line, or via a cellular wireless link.

The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. Multiple excitatory stimulation pulses can be delivered to multiple sites during a cardiac cycle in order to both pace the heart in accordance with a bradycardia mode and provide additional excitation to selected sites.

3. Delivery of Intermittent Stress Augmentation Pacing

The device shown in FIG. 1 can be configured to deliver intermittent stress augmentation pacing in a number of different ways. In one embodiment, which may be suitable for patients who need neither bradycardia nor resynchronization pacing, the device is programmed to deliver no pacing therapy at all except at periodic intervals (e.g., for five minutes each day). The pacing therapy may then be delivered in any selected pacing mode such as right ventricle-only, left ventricle-only, or biventricular pacing. In certain patients who are implanted with a pacemaker, intermittent pacing may occur fortuitously if the patient is relatively chronotropically competent and without AV block and if the programmed escape intervals of the pacemaker are long enough. In order to reliably provide augmented stress pacing and a cardioprotective effect, however, the pacemaker should be programmed so that the pacing is delivered irrespective of the patient's intrinsic rate at scheduled intervals. Other embodiments, which may be suitable for patients who need bradycardia and/or resynchronization pacing, deliver intermittent stress augmentation pacing by intermittently varying the spatial distribution of the pacing pulses applied by intermittently switching from a normal operating mode to one or more stress augmentation pacing modes. Switching to a stress augmentation mode may include altering the device's pacing pulse output configuration and/or pulse output sequence in order to initially excite different myocardial regions and thereby cause later excitation of different regions distal to the pacing site or sites, where the pulse output configuration specifies a specific subset of the available electrodes to be used for delivering pacing pulses and the pulse output sequence specifies the timing relations between the pulses. The pulse output configuration is defined by the controller selecting particular pacing channels for use in outputting pacing pulses and by selecting particular electrodes for use by the channel with switch matrix 70. If the normal operating mode is a primary pacing mode for delivering ventricular pacing therapy, the stress augmentation mode may then excite the ventricular myocardium at a site or sites different from the primary pacing mode in order to vary the spatial pattern of depolarization and cause a particular myocardial region to experience increased mechanical stress. Intermittent spatial variation in pacing may be produced, for example, by intermittently switching from a left ventricle-only pacing mode to a right ventricle-only pacing mode or vice-versa, intermittently switching from a biventricular or other multiple ventricular pacing mode to a single ventricle pacing mode or vice-versa. Spatial variation in pacing may also be produced by employing a bipolar pacing lead with electrodes spaced relatively far apart and then intermittently switching from unipolar to bipolar pacing or vice-versa, or intermittently interchanging which electrodes of the bipolar lead are the cathode and anode during bipolar pacing.

By the use of multiple pacing electrodes located at different pacing sites, a number of stress augmentation modes may be intermittently switched to in order to provide augmented stress to multiple myocardial regions. Each such stress augmentation mode may be defined by a certain pulse output configuration and pulse output sequence, and delivery of intermittent stress augmentation may involve temporarily switching to each mode according to a programmed schedule, where the device remains in the stress augmentation mode for a specified time period, referred to as the stress augmentation period (e.g., 5 minutes). By appropriate placement of the pacing electrodes, a cardioprotective effect may be provided to a large area of the ventricular myocardium. Such multiple pacing sites may be provided by multiple leads or by leads having multiple electrodes incorporated therein. For example, a multiple-electrode lead may be threaded into the coronary sinus in order to provide multiple left ventricular pacing sites. In one embodiment, stress augmentation pacing is delivered during each cardiac cycle as multi-site pacing through a plurality of the multiple electrodes. In another embodiment, the stress augmentation pacing is delivered as single-site pacing where the pacing site may be alternated between the multiple electrodes during successive cardiac cycles or during different stress augmentation periods. A switch to a stress augmentation mode may also include adjusting one or more pacing parameters such as the escape intervals that determine pacing rate in order to ensure that the stress augmentation paces are not inhibited by intrinsic cardiac activity.

As described above, the device controller may be programmed to intermittently switching from a normal operating mode to a stress augmentation mode. In the normal operating mode, the device may either deliver no therapy at all or may deliver a pacing therapy in a primary pacing mode with a different pacing configuration, a different pulse output sequence, and/or different pacing parameter settings from that of the stress augmentation mode. The device may be equipped with a single ventricular pacing channel or with multiple ventricular pacing channels each having a pacing electrode disposed at a different pacing site. In one example, the stress augmentation mode then uses at least one pacing channel not used in the primary pacing mode. The device initiates stress augmentation pacing upon receiving a command to switch to the stress augmentation mode for a specified period of time, where such a command may be generated internally according to a defined schedule, received from an external programmer, or received via a patient management network. Once the command is received, the device may then simply switch to the stress augmentation mode for a specified period of time where the pacing parameters are predefined values. For example, the stress augmentation pacing may be delivered to the ventricles in an atrial triggered synchronous mode (e.g., DDD or VDD) with predefined atrio-ventricular (AV) and ventricular-ventricular (VV) escape intervals or in a non-atrial triggered ventricular pacing mode (e.g., VVI) with a pre-defined VV escape interval where the length of the escape intervals may be set to values which result in a high pacing frequency. It may be desirable, however, to incorporate additional steps into the algorithm before switching. For example, the escape intervals for the stress augmentation mode may be dynamically determined before the mode switch in order to ensure a high pacing frequency. In an embodiment where the stress augmentation mode is a non-atrial triggered pacing mode, the device may measure the patient's intrinsic heart rate before the mode switch and then set the VV escape interval so that the pacing rate for the stress augmentation mode is slightly higher than the intrinsic rate. If the patient is receiving rate-adaptive ventricular pacing therapy in the primary pacing mode, the VV escape interval for the stress augmentation mode may be similarly modulated by an exertion level measurement. In an embodiment where the stress augmentation pacing is delivered in an atrial triggered pacing mode, the device may measure the patient's intrinsic AV interval before the mode switch (e.g., as an average over a number of cycles preceding the mode switch) so that the AV escape interval for delivering ventricular pacing can be set to pace the ventricles at a high frequency during the stress augmentation period It may also be desirable in certain patients for the device to check the patient's exertion level before switching to the stress augmentation mode and cancel the mode switch if the exertion level is above a certain threshold. This may be the case if the patient's ventricular function is somewhat compromised by the stress augmentation pacing. The device may also measure the patient's intrinsic AV interval before the mode switch (e.g., as an average over a number of cycles preceding the mode switch) so that the AV escape interval for delivering ventricular pacing in an atrial triggered mode can be set to pace the ventricles at a high frequency during the stress augmentation period.

Figure 2:
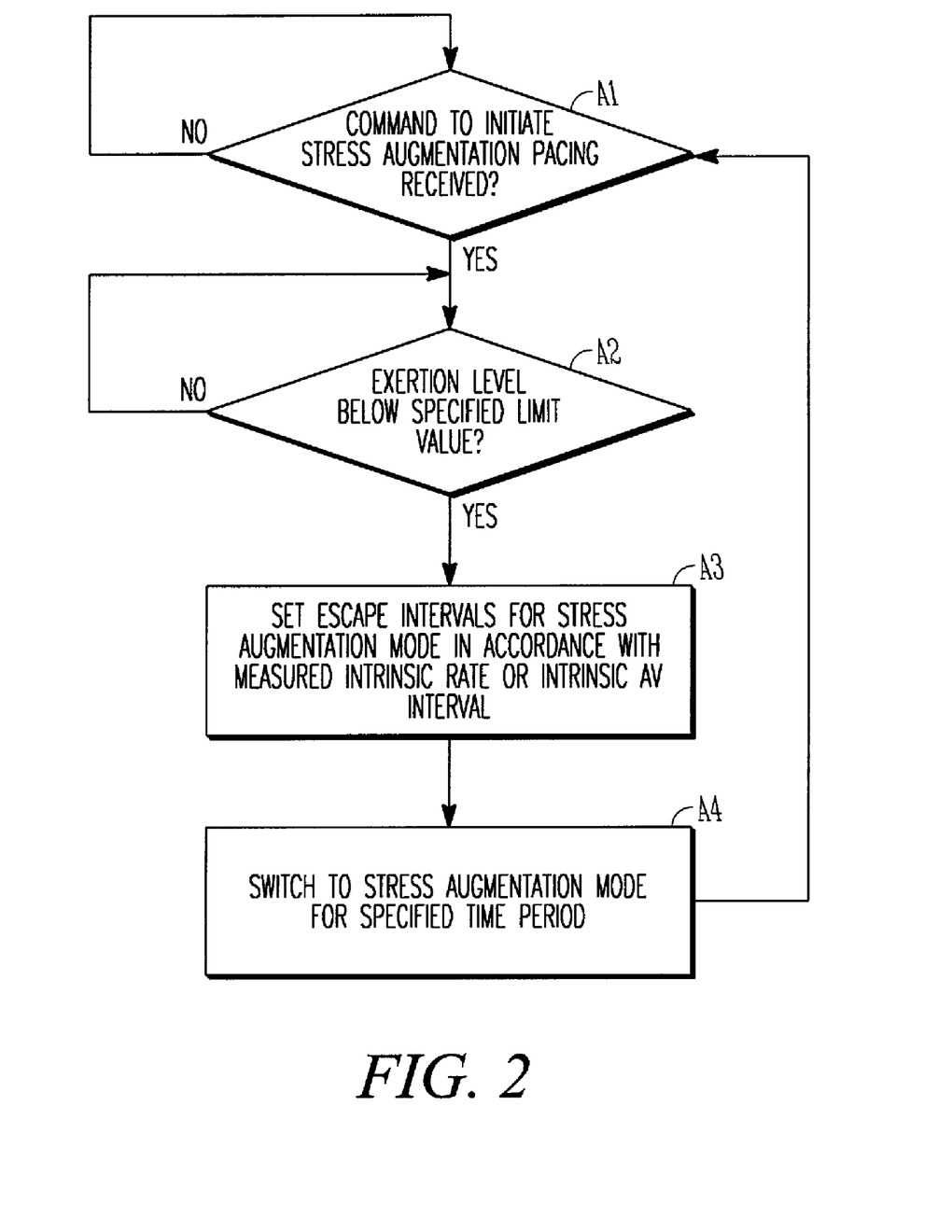
FIG. 2 illustrates an exemplary algorithm for implementing intermittent stress augmentation pacing.

FIG. 2 illustrates an exemplary algorithm for delivering stress augmentation pacing. At step A1, the device waits for a command to switch to the stress augmentation mode. Upon receiving the command, the present exertion level is checked against a specified limit value at step A2. If the exertion level is below the limit value, the device next sets the AV delay and VV escape intervals for stress augmentation pacing in an atrial triggered pacing mode at step A3, where the escape intervals are set in accordance with the patient's currently measured heart rate or intrinsic AV interval. At step A4, the device then switches to the stress augmentation mode for a specified period of time.

4. Other Embodiments

Stress augmentation pacing, as described above, exerts its cardioprotective effect by subjecting particular regions of the myocardium to increased mechanical stress for brief periods of time as compared with the stress otherwise experienced by those regions in either a primary pacing mode or during normal intrinsic contractions. Although it is believed that stress augmentation pacing does not cause ischemia in the stressed regions under normal conditions, it may nonetheless be desirable to inhibit a switch to a stress augmentation mode if the patient is presently experiencing some degree of cardiac ischemia. Accordingly, the device may be configured to detect cardiac ischemia from a morphology analysis of an electrogram collected during an intrinsic or a paced beat, the latter sometimes referred to as an evoked response. The electrogram for detection of ischemia is recorded from a sensing channel that senses the depolarization and repolarization of the myocardium during a cardiac cycle. The sensing channel used for this purpose may be a sensing channel used for detecting cardiac arrhythmias and/or intrinsic beats or may be a dedicated channel. In order to detect ischemic changes in an electrogram, it may be preferable to record the electrogram with a unipolar electrode that "sees" a larger volume of the myocardium as a wave of electrical activity spreads than a bipolar electrode. In order to detect an ischemic change, the electrogram can be compared with a reference electrogram to see if an increased current of injury is present. The comparison may involve, for example, cross-correlating the recorded and reference electrograms or comparing ST segment amplitudes, slopes, or integrations with reference values.

In order to detect whether the patient is experiencing cardiac ischemia during pacing, the controller is programmed to analyze the recorded electrogram of an evoked response and look for a "current of injury." When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury may be produced by an infarcted region that becomes permanently depolarized or by an ischemic region that remains abnormally depolarized during all or part of the cardiac cycle. A current of injury results in an abnormal change in the electrical potentials measured by either a surface electrocardiogram or an intracardiac electrogram. If the abnormal depolarization in the ventricles lasts for the entire cardiac cycle, a zero potential is measured only when the rest of the ventricular myocardium has depolarized, which corresponds to the time between the end of the QRS complex and the T wave in an electrogram and is referred to as the ST segment. After repolarization of the ventricles, marked by the T wave in an electrogram, the measured potential is influenced by the current of injury and becomes shifted, either positively or negatively depending upon the location of the ischemic or infarcted region, relative to the ST segment. Traditionally, however, it is the ST segment that is regarded as shifted when an abnormal current of injury is detected by an electrogram or electrocardiogram. A current injury produced by an ischemic region that does not last for the entire cardiac cycle may only shift part of the ST segment, resulting in an abnormal slope of the segment. A current of injury may also be produced when ischemia causes a prolonged depolarization in a ventricular region which results in an abnormal T wave as the direction of the wave of repolarization is altered.

Figure 3:
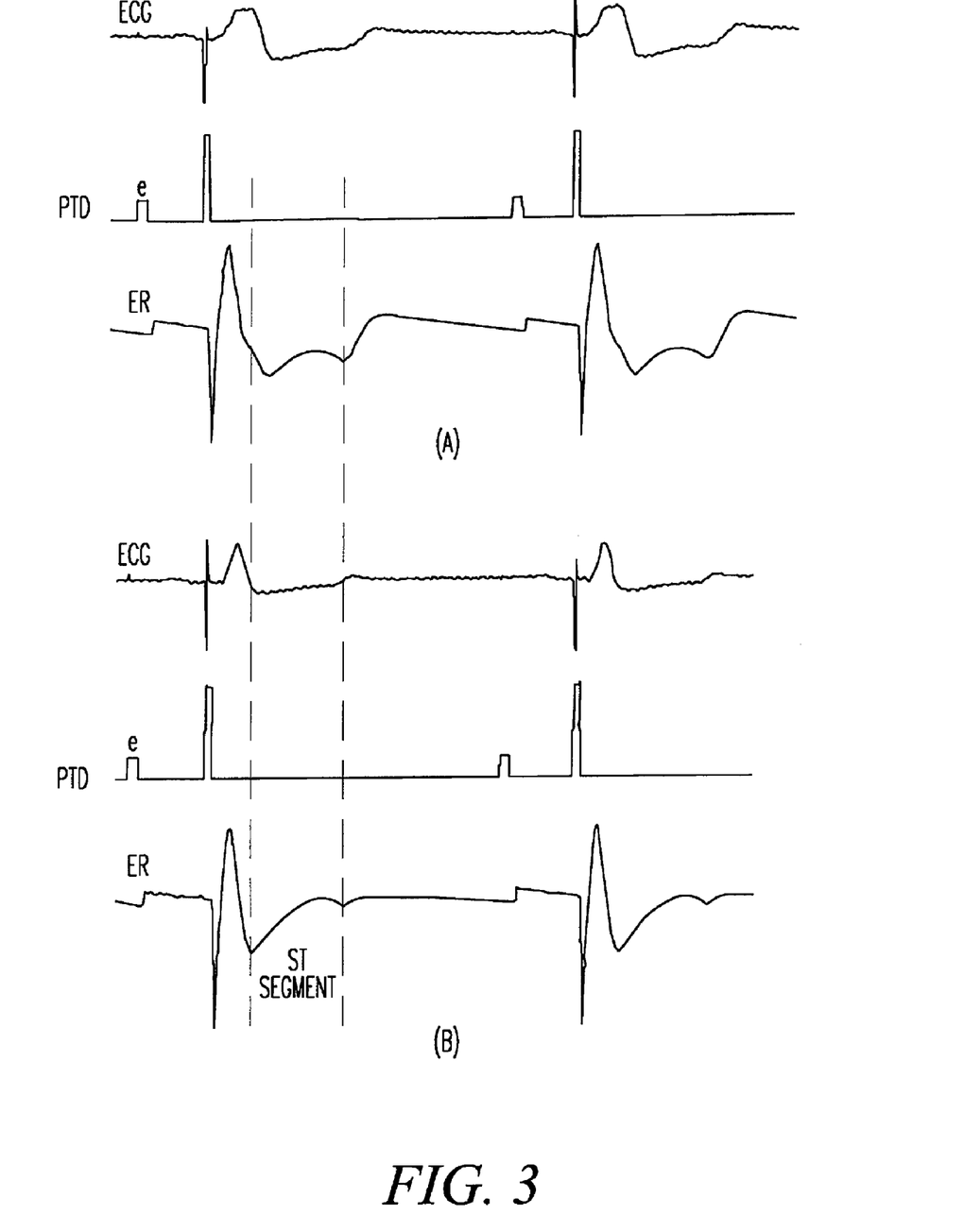
FIG. 3 illustrates ischemic changes in a recorded electrogram.

In order to detect a change in an electrogram indicative of ischemia, a recorded electrogram is analyzed and compared with a reference electrogram, which may either be a complete recorded electrogram or particular reference values representative of an electrogram. Because certain patients may always exhibit a current of injury in an electrogram (e.g., due to CAD or as a result of electrode implantation), the controller is programmed to detect ischemia by looking for an increased current of injury in the recorded electrogram as compared with the reference electrogram, where the latter may or may not exhibit a current of injury. FIG. 3 shows examples of evoked response data for two cases labeled A and B, where A is the baseline reference and B is during an acute ischemic episode. A surface electrocardiogram labeled ECG, a pacing timing diagram labeled PTD, and an electrogram labeled ER are illustrated for each case. The ST segment of the electrogram for case B is seen to have different amplitudes and slopes as compared with the amplitudes and slopes of the ST segment of the electrogram for case A. One way to look for an increased current of injury in the recorded electrogram is to compare the ST segment amplitude and/or slope with the amplitude and slope of a reference electrogram. Various digital signal processing techniques may be employed for the analysis, such as using first and second derivatives to identify the start and end of an ST segment. Other ways of looking for a current injury may involve, for example, cross-correlating the recorded and reference electrograms to ascertain their degree of similarity. The electrogram could be implicitly recorded in that case by passing the electrogram signal through a matched filter that cross-correlates the signal with a reference electrogram. The ST segment could also be integrated, with the result of the integration compared with a reference value to determine if an increased current of injury is present.

If a change in a recorded electrogram indicative of ischemia is detected, the controller may be programmed to inhibit switching to a stress augmentation pacing mode. Detection of cardiac ischemia may also be logged as a clinically significant event in the pacemaker's memory, where the event log and/or the recorded electrogram exhibiting the ischemia may then be later downloaded to a clinician for analysis via an external programmer. Information derived from other analyses or other sensing modalities may also be used to more specifically detect cardiac ischemia. For example, dyspnea or other abnormal breathing patterns may be detected using a minute ventilation sensor by programming the controller to compare the transthoracic impedance signal from the sensor with a template representing the abnormal pattern.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
a pulse generator for delivering pacing pulses to a selected ventricular myocardial site through a pacing channel;
a controller for controlling the delivery of pacing pulses in accordance with a programmed pacing mode,
wherein the controller is programmed to operate in either a normal operating mode or a stress augmentation mode in which a particular region or regions of the ventricular myocardium are subjected to increased mechanical stress as compared with the stress experienced by those regions during the normal operating mode; and,
wherein the controller is further programmed to intermittently switch from the normal operating mode to the stress augmentation mode for a specified stress augmentation time period according to a defined schedule.

2. The device of claim 1 wherein the normal operating mode is a primary pacing mode for delivering ventricular pacing therapy and wherein stress augmentation mode causes a different depolarization pattern than the primary pacing mode.

3. The device of claim 2 wherein the stress augmentation mode excites the ventricular myocardium at a site or sites different from the primary pacing mode.

4. The device of claim 2 wherein the switch from a primary pacing mode to a stress augmentation mode involves switching from bipolar pacing to unipolar pacing or vice-versa.

5. The device of claim 2 wherein the switch from a primary pacing mode to a stress augmentation mode involves switching which electrode of a bipolar pacing lead is the cathode and which electrode is the anode.

6. The device of claim 2 further comprising:
multiple pulse generators for delivering pacing pulses to a plurality of ventricular pacing sites through multiple pacing channels; and,
wherein the stress augmentation mode uses at least one pacing channel not used in the primary pacing mode.

7. The device of claim 6 wherein the switch from a primary pacing mode to a stress augmentation mode involves switching from left ventricle-only pacing to right ventricular pacing or vice-versa.

8. The device of claim 6 wherein the switch from a primary pacing mode to a stress augmentation mode involves switching from biventricular pacing to single ventricular pacing or vice-versa.

9. The device of claim 1 further comprising an exertion level sensor and wherein the controller is programmed such that the switch from a normal operating mode to a stress augmentation mode is inhibited if the measured exertion level is above a specified limit value.

10. The device of claim 1 further comprising a sensing amplifier for incorporation into a cardiac sensing channel and wherein the controller is programmed to detect cardiac ischemia from an electrogram morphology analysis and further wherein the controller is programmed such that the switch from a normal operating mode to a stress augmentation mode is inhibited if cardiac ischemia is detected.

11. A method for operating a cardiac rhythm management device, comprising:
delivering pacing therapy in either a normal operating mode or a stress augmentation mode in which a particular region or regions of the ventricular myocardium are subjected to increased mechanical stress as compared with the stress experienced by those regions during the normal operating mode;
intermittently switching from the normal operating mode to the stress augmentation mode for a specified stress augmentation time period according to a defined schedule.

12. The method of claim 11 wherein the normal operating mode is a primary pacing mode for delivering ventricular pacing therapy and wherein stress augmentation mode causes a different depolarization pattern than the primary pacing mode.

13. The method of claim 12 wherein the stress augmentation mode excites the ventricular myocardium at a site or sites different from the primary pacing mode.

14. The method of claim 12 wherein the switch from a primary pacing mode to a stress augmentation mode involves switching from bipolar pacing to unipolar pacing or vice-versa.

15. The method of claim 12 wherein the switch from a primary pacing mode to a stress augmentation mode involves switching which electrode of a bipolar pacing lead is the cathode and which electrode is the anode.

16. The method of claim 12 wherein the device is equipped with multiple pacing channels and further wherein the stress augmentation mode uses at least one pacing channel not used in the primary pacing mode.

17. The method of claim 16 wherein the switch from a primary pacing mode to a stress augmentation mode involves switching from left ventricle-only pacing to right ventricular pacing or vice-versa.

18. The method of claim 16 wherein the switch from a primary pacing mode to a stress augmentation mode involves switching from biventricular pacing to single ventricular pacing or vice-versa.

19. The method of claim 11 further comprising measuring a patient's exertion level inhibiting the switch from a normal operating mode to a stress augmentation mode if the measured exertion level is above a specified limit value.

20. The method of claim 11 further comprising detecting cardiac ischemia from an electrogram morphology analysis and inhibiting the switch from a normal operating mode to a stress augmentation mode if cardiac ischemia is detected.

* * * * *